United States Patent
Kroon et al.

(10) Patent No.: US 9,516,823 B2
(45) Date of Patent: Dec. 13, 2016

(54) PLASMODIOPHORA BRASSICAE-RESISTANT BRASSICA PLANT, SEEDS AND PLANT PARTS THEREOF AND METHODS FOR OBTAINING THE SAME

(75) Inventors: Laurentius Petrus Nicolaas Martinus Kroon, Alkmaar (NL); Albertus Johannes Maria Schrijver, Warmenhuizen (NL); Roelof Marinus Veenstra, Wieringerwaard (NL); Klaas Biersteker, Sint Pancras (NL)

(73) Assignee: BEJO ZADEN B.V., Warmenhuizen (NL)

( * ) Notice: Subject to any disclaimer, the term of this patent is extended or adjusted under 35 U.S.C. 154(b) by 268 days.

(21) Appl. No.: 13/989,977

(22) PCT Filed: Nov. 28, 2011

(86) PCT No.: PCT/EP2011/071190
§ 371 (c)(1),
(2), (4) Date: Jul. 12, 2013

(87) PCT Pub. No.: WO2012/072584
PCT Pub. Date: Jun. 7, 2012

(65) Prior Publication Data
US 2013/0305407 A1    Nov. 14, 2013

(30) Foreign Application Priority Data
Nov. 29, 2010   (NL) ..................... 2005777

(51) Int. Cl.
*A01H 1/02* (2006.01)
*C12Q 1/68* (2006.01)
*A01H 5/10* (2006.01)

(52) U.S. Cl.
CPC *A01H 1/02* (2013.01); *A01H 5/10* (2013.01); *C12Q 1/6895* (2013.01)

(58) Field of Classification Search
None
See application file for complete search history.

(56) References Cited

PUBLICATIONS

Voorrips et al., 1997, Theoretical and Applied Genetics 94: 75-82.*
Voorrips et al., 1997, Theor Appl. Genet. 94: 75-82.*
Piao et al., 2009, J. Plant Growth Regul. 28: 252-264.*
Batley and Edwards, 2007, In: Association Mapping in Plants, pp. 95-102.*
Grandclément and Thomas, 1996, Theor. Appl. Genet. 93: 86-90.*
Voorrips, R.E. et al., "Mapping of two genes for resistance to clubroot (Plasmodiophora brassicae) in a population of doubled haploid lines of Brassica oleracea by means of RFLP and AFLP markers," Theor Appl Genet, 1997, pp. 75-82, vol. No. 94, Springer-Verlag.

* cited by examiner

*Primary Examiner* — David T Fox
*Assistant Examiner* — Bratislav Stankovic
(74) *Attorney, Agent, or Firm* — Nath, Goldberg & Meyer; Joshua B. Goldberg; Scott H. Blackman

(57) ABSTRACT

The present invention relates to a *Plasmodiophora brassicae*-resistant *Brassica* plant. The present invention relates more specifically to a *Plasmodiophorabrassicae*-resistant *Brassica* plant comprising in its genome two or more genetic factors imparting resistance, where in the presence of the genetic factors imparting resistance can be determined by the presence of a Quantitative Trait Locus (QTL1) and a Quantitative Trait Locus (QTL3) and/or a Quantitative Trait Locus 5 (QTL5).

7 Claims, No Drawings

PLASMODIOPHORA BRASSICAE-RESISTANT BRASSICA PLANT, SEEDS AND PLANT PARTS THEREOF AND METHODS FOR OBTAINING THE SAME

This is a National Phase Application filed under 35 U.S.C. §371 as a national stage of International Application No. PCT/EP2011/071190, filed on Nov. 28, 2011, claiming the benefit from Netherland Patent Application No. 2005777, filed on Nov. 29, 2010, the content of each of which is hereby incorporated by reference in its entirety.

The Sequence Listing submitted in text format (.txt) filed on May 28, 2013, named, "SequenceListing_2LT68.txt," (created on May 13, 2013, 7 KB), is incorporated herein by reference.

The present application relates to a *Plasmodiophora brassicae*-resistant *Brassica* plant, in particular a *Plasmodiophora brassicae*-resistant *Brassica oleracea* plant and to seeds, fruits and/or plant parts thereof. According to a further aspect, the invention relates to methods for obtaining *Plasmodiophora brassicae*-resistant *Brassica* plants. In addition, the present invention relates to Quantitative Trait Loci (QTLs) which provide the present *Plasmodiophora brassicae* resistance and molecular markers, in particular Random Amplified Microsatellite Polymorphism (RAMP) markers, for identifying the present Quantitative Trait Loci (QTLs).

The soil-bound micro-organism *Plasmodiophora brassicae* is the cause of clubroot in crucifers (Brassicaceae). *Brassica* is a plant genus in the family Brassicaceae (formerly Cruciferae). The members of this genus are collectively referred to as cabbage or mustard. The genus *Brassica* comprises a number of important agricultural and horticultural crops, including rape, cauliflower, red cabbage, savoy cabbage, white cabbage, oxheart cabbage, curly cale cabbage, broccoli, Brussels sprouts, Chinese cabbage, turnip cabbage and Portuguese cabbage (*tronchuda*).

Almost all parts of the plants are used as food, such as the roots (turnip), stalks (turnip cabbage), leaves (white and red cabbage, savoy cabbage), axillary buds (sprouts), flowers (cauliflower, broccoli), seedlings and seeds (rape). Some species with white or purple flowers or distinct colour or shape of the leaves are further cultivated for ornamental purposes.

Infestation by *Plasmodiophora brassicae* takes place via the root hairs of cabbage plants. When a zoospore of *Plasmodiophora brassicae* has penetrated the root, this spore induces the cells around the infection site to hypertrophy (cell enlargement) and hyperplasia (cell division). The hormonal stimulus for these processes diffuses further in the plant, so that these structural changes can also take place in non-affected cells.

*Plasmodiophora brassicae* does not form hyphae in the plant, but appears in the form of a *plasmodium* which occurs intracellularly in the tissue. This *plasmodium* brings about further damage to the roots by forming zoosporangia, from which new zoospores are released. The disease is characterized by highly swollen roots which, in the further progress of the disease process, fall apart due to rotting. The formed oospores of the pathogen are released here in the ground. Above-ground parts of the host plant further lag behind in growth because of an impeded water and mineral take-up due to the damaged root system.

It is assumed that 10% of the cabbage-growing area world-wide is infected with *Plasmodiophora brassicae*. This results in considerable annual loss of yield.

In view of the importance of *Brassica* plants for food production and the economic damage caused by the pathogen *Plasmodiophora brassicae*, the present invention has for its object to provide a *Plasmodiophora brassicae*-resistant *Brassica* plant and methods for obtaining same.

The need for a *Plasmodiophora brassicae*-resistant *Brassica* plant for food production is further underlined by the absence of adequate, cost effective and efficient means of combatting this disease, such as the unavailability of pesticides for this pathogen. *Plasmodiophora brassicae* is one of the most important pathogens on crucifers world-wide.

The above stated object of the present invention, among others, is achieved according to a first aspect by providing a *Plasmodiophora brassicae*-resistant *Brassica* plant as according to the appended claim 1.

The above stated object of the present invention, among others, is specifically provided according to a first aspect by a *Plasmodiophora brassicae*-resistant *Brassica* plant comprising in its genome two or more genetic factors imparting resistance, wherein the presence of the genetic factors imparting resistance can be determined by the presence of a Quantitative Trait Locus 1 (QTL1) and a Quantitative Trait Locus 3 (QTL3) and/or a Quantitative Trait Locus 5 (QTL5), wherein Quantitative Trait Locus 1 (QTL1) is characterized by one or more RAMP markers chosen from the group consisting of a fragment of 292-296 bp with primer combination SEQ ID No:1 (1.1) and 7; a fragment of 69-73 bp with primer combination SEQ ID No:2 (1.2) and 7; a fragment of 113-117 bp with primer combination SEQ ID No:3 (1.3) and 7; a fragment of 214-217 bp or 215-219 bp with primer combination SEQ ID No:4 (1.4) and 7 and a fragment of 201-205 bp with primer combination SEQ ID No: 24 (1.5) and 7;

Quantitative Trait Locus 3 (QTL3) is characterized by one or more RAMP markers chosen from the group consisting of a fragment of 157-169 bp with primer combination SEQ ID No:9 (3.1) and 7; a fragment of 133-137 bp with primer combination SEQ ID No:10 (3.2) and 7; a fragment of 218-222 bp with primer combination SEQ ID No:11 (3.3) and 7; and a fragment of 73-77 bp with primer combination SEQ ID No:12 (3.4) and 7;

Quantitative Trait Locus 5 (QTL5) is characterized by one or more RAMP markers chosen from the group consisting of a fragment of 274-278 bp with primer combination SEQ ID No:16 (5.1) and 7; a fragment of 533-537 bp with primer combination SEQ ID No:17 (5.2) and 7; a fragment of 333-341 bp with primer combination SEQ ID No:18 (5.3) and 7; and a fragment of 217-225 bp with primer combination SEQ ID No:19 (5.4) and 7.

It should be noted that in accordance with the above definition of a plant according to the present invention, the present invention relates to *Brassica* plants comprising QTL1 and QTL3, plants comprising QTL1 and QTL5 and plants comprising QTL1, QTL3 and QTL5.

According to this first aspect of the present invention a *Plasmodiophora brassicae*-resistant *Brassica* plant is provided. The present plant comprises a resistance to all four pathotypes of *Plasmodiophora brassicae*. In other words, the present plant comprises resistance to the *Plasmodiophora brassicae* pathotypes 0, I, II and III.

The primer no. 7 as used in the present context is a commercially available RAPD primer (Operon RAPD 10-mer kits A-01 up to and including BH-20).

According to a preferred embodiment of the present invention, the present plant comprises in its genome the Quantitative Trait Locus 1 (QTL1) and the Quantitative Trait Locus 3 (QTL3) and/or the Quantitative Trait Locus 5 (QTL5) as defined above.

According to a further preferred embodiment, the present plant is homozygous for the Quantitative Trait Locus (QTL1), the Quantitative Trait Locus 3 (QTL3) and/or the Quantitative Trait Locus 5 (QTL5).

According to another preferred embodiment of the invention, the present plant also comprises in its genome three or more factors imparting resistance, wherein the presence of the genetic factors imparting resistance can be determined by the presence of a Quantitative Trait Locus 2 (QTL2), a Quantitative Trait Locus 4 (QTL4) and/or a Quantitative Trait Locus 6 (QTL6), wherein Quantitative Trait Locus 2 (QTL2) is characterized by one or more RAMP markers chosen from the group consisting of a fragment of 740-750 bp with primer combination SEQ ID No:5 (2.1) and 7; a fragment of 141-145 bp with primer combination SEQ ID No:6 (2.2) and 7; a fragment of 167-171 bp with primer combination SEQ ID No:7 (2.3) and 7; and a fragment of 293-297 bp with primer combination SEQ ID No:8 (2.4) and 7;

Quantitative Trait Locus 4 (QTL4) is characterized by one or more RAMP markers chosen from the group consisting of a fragment of 314-318 bp with primer combination SEQ ID No:13 (4.1) and 7; a fragment of 240-244 bp with primer combination SEQ ID No:14 (4.2) and 7; and a fragment of 112-116 bp with primer combination SEQ ID No:15 (4.3) and 7; and Quantitative Trait Locus 6 (QTL6) is characterized by one or more RAMP markers chosen from the group consisting of a fragment of 201-205 bp with primer combination SEQ ID No:20 (6.1) and 7; a fragment of 291-295 bp with primer combination SEQ ID No:21 (6.2) and 7; a fragment of 183-187 bp with primer combination SEQ ID No:22 (6.3) and 7; and a fragment of 375-379 bp with primer combination SEQ ID No:23 (6.4) and 7.

It should be noted that in accordance with the above definition of a plant according to the present invention, the present invention relates to *Brassica* plants comprising QTL1 and QTL3, plants comprising QTL1 and QTL5 and plants comprising QTL1, QTL3 and QTL5 and said plant further comprise QTL2, QTL4 or QTL6, thus plants comprising QTL1, QTL3 and QTL2; QTL1, QTL3 and QTL4; QTL1, QTL3 and QTL6; plants comprising QTL1, QTL5 and QTL2; QTL1, QTL5 and QTL4; QTL1, QTL5 and QTL6 and plants comprising QTL1, QTL3, QTL5 and QTL2; QTL1, QTL3, QTL5 and QTL4; QTL1, QTL3, QTL5 and QTL6; and plants comprising QTLs 1 to 6 or 1 to 5 or 1 to 4.

According to another preferred embodiment, the plant according to the invention further comprises in its genome the Quantitative Trait Locus 2 (QTL2), the Quantitative Trait Locus 4 (QTL4) and/or the Quantitative Trait Locus 6 (QTL6) as defined above.

According to a preferred embodiment of the invention, the present Quantitative Trait Locus 1 (QTL1), 2 (QTL2), 3 (QTL3), 4 (QTL4), 5 (QTL5) and/or 6 (QTL6) are characterized by two or more RAMP markers per marker as defined above.

According to a preferred embodiment of the invention, the present Quantitative Trait Locus 1 (QTL1), 2 (QTL2), 3 (QTL3), 4 (QTL4), 5 (QTL5) and/or 6 (QTL6) are characterized by three or more RAMP markers per QTL as defined above.

According to a preferred embodiment of the invention, the present Quantitative Trait Locus 1 (QTL1), (QTL2), 3 (QTL3), 5 (QTL5) and/or 6 (QTL6) are characterized by four or more RAMP markers per QTL as defined above.

According to an especially preferred embodiment of the present invention, the presence of present QTL1 is indicated by 5 RAMP markers as defined above.

According to still an especially preferred embodiment, the presence of the present QTLs is indicated by all markers defined.

According to a preferred embodiment of the present invention, the plant is a *Brassica oleracea* plant.

According to a further preferred embodiment of the present invention, the plant is a *Brassica* plant chosen from the group consisting of *B. oleracea* convar. *botrytis* var. *botrytis* (cauliflower, romanesco broccoli), *B. oleracea* convar. *botrytis* var. *cymosa* (broccoli), *B. oleracea* convar. *botrytis* var. *asparagoides* (sprouting broccoli), *B. oleracea* convar. *oleracea* var. *gemmifera* (Brussels sprout), *B. oleracea* convar. *capitata* var. *alba* (white cabbage, oxheart cabbage), *B. oleracea* convar. *capitata* var. *rubra* (red cabbage), *B. oleracea* convar. *capitata* var. *sabauda* (savoy cabbage), *B. oleracea* convar. *acephala* var. *sabellica* (curly cale cabbage), *B. oleracea* convar. *acephala* var. *gongyloides* (turnip cabbage) and *B. oleracea* var. *tronchuda* syn. *costata* (Portuguese cabbage).

The plants according to the present invention as outlined above preferably have a *Plasmodiophora brassicae*-resistance derived from a plant with deposit number NCIMB 41685 or NCIMB 41686 obtainable from NCIMB Ltd, Ferguson Building, Craibstone Estate, Bucksburn, Aberdeen AB21 9YA, England.

The plants according to the present invention as outlined above preferably have a *Plasmodiophora brassicae*-resistance which is found in plants with deposit number NCIMB 41685 or NCIMB 41686 obtainable from NCIMB Ltd, Ferguson Building, Craibstone Estate, Bucksburn, Aberdeen AB21 9YA, England.

The plants according to the present invention as outlined above preferably are derived from a plant with the deposit number NCIMB 41685 or NCIMB 41686 obtainable from NCIMB Ltd, Ferguson Building, Craibstone Estate, Bucksburn, Aberdeen AB21 9YA, England.

An advantageous plant according to the present invention is a plant with deposit number NCIMB 41685 or NCIMB 41686, obtainable from NCIMB Ltd, Ferguson Building, Craibstone Estate, Bucksburn, Aberdeen AB21 9YA, England.

In view of the advantageous present resistance of the *Brassica* plant according to the invention, the invention also relates according to a further aspect to seeds, fruits and/or plant parts of the present *Brassica* plant which comprise the Quantitative Trait Locus 1 (QTL1) and the Quantitative Trait Locus 3 (QTL3) and/or the Quantitative Trait Locus 5 (QTL5) as defined above.

According to an embodiment of this aspect, the seeds, fruits and/or plant parts of the present *Brassica* plant also comprise the Quantitative Trait Locus 2 (QTL2), the Quantitative Trait Locus 4 (QTL4) and/or the Quantitative Trait Locus 6 (QTL6) as defined above.

According to a further aspect, the present invention also relates to a method for providing a *Plasmodiophora brassicae*-resistant *Brassica oleracea* comprising introgression, or the genomic combination, of the Quantitative Trait Locus 1 (QTL1) and the Quantitative Trait Locus 3 (QTL3) and/or the Quantitative Trait Locus 5 (QTL5) as defined above, in a *Brassica* plant.

According to a particularly recommended embodiment of this aspect, the method further comprises of introgression, or genomic combining, of the Quantitative Trait Locus 2 (QTL 2), the Quantitative Trait Locus 4 (QTL 4) and/or the Quantitative Trait Locus 6 (QTL 6) as defined above in a *Brassica* plant.

According to another preferred embodiment of this aspect, the present method further comprises molecular biological techniques for determining the presence of one or more of the RAMP markers as defined above in a *Brassica* plant.

According to a preferred embodiment of this aspect, the *Brassica* plant is homozygous for the Quantitative Trait Loci 1 (QTL1), 3 (QTL3) and 5 (QTL5).

According to yet another aspect, the present invention relates to the use of a Quantitative Trait Locus 1 (QTL1), 2 (QTL2), 3 (QTL3), 4 (QTL4), 5 (QTL5) and/or 6 (QTL6) as defined above for providing a *Plasmodiophora brassicae*-resistant *Brassica* plant, preferably a *Brassica oleracea* plant, such as a plant according to the present invention.

According to yet another aspect, the present invention relates to the use of one or more primers selected from the group consisting of SEQ ID NOs: 1-24 (primers 1.1, 1.2, 1.3, 1.4, 1.5, 2.1, 2.2, 2.3, 2.4, 3.1, 3.2, 3.3, 3.4, 4.1, 4.2, 4.3, 5.1, 5.2, 5.3, 5.4, 6.1, 6.2, 6.3, and 6.4) for providing a *Plasmodiophora brassicae*-resistant *Brassica* plant, such as a plant according to the present invention.

According to yet another aspect, the present invention relates to the use of a plant according to the present invention, or of seeds, fruits and/or plant parts according to the present invention for providing a *Plasmodiophora brassicae*-resistant *Brassica* plant.

The present invention will be further described hereinbelow on the basis of an example of a preferred embodiment. It should however be understood that this example is provided solely for illustrative purposes and not to limit in any way the invention as described above.

EXAMPLE

The breeding aimed at *Plasmodiophora brassicae* resistance in *Brassica oleracea* is a complex process. Multiple pathotypes of *Plasmodiophora brassicae* have been described and resistance occurs only rarely in *Brassica oleracea*.

In order to obtain the *Brassica oleracea* plant described here with a broad resistance to *Plasmodiophora brassicae* use is made of a genetic source having a dominant resistance. In addition, a genetic source is used in which the resistance is determined multigenically. Via a backcrossing program the resistances are introduced into various genetic backgrounds (susceptible parent lines).

Each crossing with a susceptible plant is followed by an inbred generation. The progeny of this generation must be tested in a greenhouse test for their resistance level. It therefore always takes a minimum of two years per generation to see the effect of a new crossing in the case of an annual plant and a minimum of 3 years in the case of a biannual plant.

The resistance tests were performed by bringing the roots of young plants into contact with a clubroot inoculum during growth and development. This inoculum was prepared, one day before the test was started, by finely grinding 150 grams of frozen cabbage roots from defined isolates with clubroot infestation and mixing this with 4000 grams of potting compost. Water was subsequently added to the mixture until it was wholly saturated. The inoculum was stored for 1 day at 20° C., so that the *P. brassicae* spores could actively spread through the soil/water mixture. On the day of inoculation, 5 day-old seedlings of the material to be tested were transplanted into 1 cc of the soil/water/*P. brassicae* mixture. For this purpose the inoculum doses were laid out shortly before the transplanting operation on a layer of 10 cm potting compost arranged in a greenhouse staging. The plants were subsequently cultivated for 6 weeks in a lit greenhouse with a day/night rhythm of respectively 16 and 8 hours and a day/night temperature of 20/16° C.

Prior to the assessment the plants were carefully harvested and washed clean. Because this does not involve a black and white resistance reaction, the level was expressed as a quantitative value {0 (wholly resistant) to 9 (wholly susceptible)}. Roots of category 9 are highly susceptible and displayed severe swelling. Roots of category 0 are wholly free of swelling. It was found that the resistance in the various genetic backgrounds did not show simple Mendelian behaviour but a phenotypic gradation within a normal distribution. This distribution can shift sharply to the susceptible side, implying that the inbred populations from crossings between the resistant source and various susceptible parent lines produce different percentages of resistant plant.

On the basis of the segregation ratios and the differences in resistance levels of the plants in the populations it was found that the resistance level of the plant is determined by multiple genetic factors. In order to map a quantitative trait with DNA markers, use is usually made of QTL analyses. QTLs are independent chromosome regions which, coupled to the underlying genes, together explain or define a trait.

Using DNA markers a genome-spanning QTL analysis was performed on *Brassica oleracea* crossing populations with diverse genetic backgrounds. Using plants of these different populations greenhouse tests were carried out in order to determine the resistance level of the individual plants. By combining the data of the marker analysis with that of the greenhouse tests scores it was possible to identify the QTLs which are responsible for the *Plasmodiophora brassicae* resistance.

A total of six independently inheritable QTLs have been identified which contribute to greater or lesser extent toward the level of resistance. The variation in the resistance levels between the plants which is observed in the greenhouse test is caused by the presence and/or absence of the QTLs. One of these can be designated the main QTL (QTL 1) which must always be present to obtain any broadly effective resistance at all.

Just as QTL 1, the QTLs 3 and 5 contribute toward the resistance level, and although this contribution is not as great as that of the main QTL it is also independent of the genetic background. The other three QTLs (QTL 2, 4 and 6) possibly have a modifying role which causes variation in resistance levels.

The use of DNA markers coupled to the QTLs 1 to 6 has made it possible to select plants which are resistant to *Plasmodiophora brassicae*. Selection of traits located at multiple regions requires large selection populations. In an inbred population made from an individual originating from a cross between a resistant and a susceptible plant, the chance is 1:64 that a plant is actually present with the three most important QTLs homozygous from the source.

Selection with DNA markers provides the option of performing repeated backcrossing wherein selection is made for the QTLs involved in clubroot resistance (Marker Assisted Recurrent Backcross, MARB). In this way one or two years are gained per crossing generation, which means an acceleration of ten to twenty years in the breeding program.

From a disease test plants with a high level of resistance could be obtained, but which have one or more QTLs in heterozygous form. The use of DNA markers provided the possibility of analysing for clubroot-resistant plants from populations in the breeding program and of making a preselection of the desired plants.

Used as starting material for this preselection were selected plants with desired horticultural quality traits. These plants were partially heterozygous; so that they could serve as parent of a hybrid variety, they had to be made wholly homozygous.

A method of making all introgressions of the QTLs in the acceptor plant homozygous was via induction of dihaploids. The method for inducing dihaploids in *Brassica* plants is described in various publications.

The ploidy level of each regenerated plant was determined (Partec CA-II, Partec, Munster) and only dihaploid plants were retained.

The QTLs are each characterized by a number of DNA markers as listed in table 2 which characterize the introgression from the source.

The DNA markers are generated with the RAMP technique. The RAMP technique, wherein an iSSR and a RAPD-primer are combined, produces band patterns having therein DNA fragments specifically co-segregating with the resistance, whereby a distinction can be made between individuals which do comprise the QTL introgression and individuals which do not comprise the QTL introgression. By mapping the RAMP fragments and phenotyping of the resistance score closely linked RAMP markers are identified which form the QTL, an overview of these markers being given in table 2. The position of the QTL on the 'linkage group' involved and the mutual distance of the markers within the QTLs are given in centimorgans (cM).

The general PCR conditions under which the DNA markers were generated are shown in the overview below.

PCR Mix for RAMP Reaction:
Per reaction
~0.2 ng/µl genomic plant DNA
75 mM Tris-HCl (pH 8.8)
20 mM $NH_4SO_4$
0.01% (v/v) Tween20
2.80 mM $MgCl_2$
0.25 mM dNTPs
0.12 µM forward-primer
0.29 µM reverse-primer
0.04 units/µl Red Hot® DNA Polymerase (ABgene, Epsom)

PCR Program RAPD35:

|  |  | Number of cycles |
|---|---|---|
| step 1: | 2 min 93° C. | 1 |
| step 2: | 30 sec 93° C. |  |
| step 3: | 30 sec 40° C. |  |
| step 4: | heat at 0.3° C./sec to 72° C. |  |
| step 5: | 1 min 30 sec 72° C. | 40 |
|  | repeat step 2-5 |  |
| step 6: | 5 min 72° C. | 1 |

PAGE/Licor

For analysis of the RAMP patterns use was made of a "Gene ReadIR 4200 DNA analyzer" (Licor Inc.). On the basis of an optimal concentration of 6.5% acryl amide, fragments can be separated down to a single base. In order to make the fragments visible on this system it is necessary to use labelled (IRDye labels) primers. For this purpose a third of the quantity of forward primer was replaced by a labeled primer with the same sequence.

Marker Overview

The primers referred to in Table 2 are used to generate the DNA markers referred to in Table 1.

TABLE 1

Overview of RAMP markers per QTL

| QTL | RAMP primer combination | Fragment size (bp) | Position on the associated 'linkage group' (cM) |
|---|---|---|---|
| 1 | 1.1 + 7 | 294 bp | 43.1 |
| 1 | 1.2 + 7 | 71 bp | 68.2 |
| 1 | 1.3 + 7 | 115 bp | 68.2 |
| 1 | 1.4 + 7 | 215 or 218 bp | 83.8 |
| 1 | 1.5 + 7 | 203 bp | 68.2 |
| 2 | 2.1 + 7 | 745 bp | 55.0 |
| 2 | 2.2 + 7 | 143 bp | 56.8 |
| 2 | 2.3 + 7 | 169 bp | 58.4 |
| 2 | 2.4 + 7 | 295 bp | 73.5 |
| 3 | 3.1 + 7 | 159 bp | 96.9 |
| 3 | 3.2 + 7 | 135 bp | 103.0 |
| 3 | 3.3 + 7 | 220 bp | 103.2 |
| 3 | 3.4 + 7 | 75 bp | 104.3 |
| 4 | 4.1 + 7 | 316 bp | 15.1 |
| 4 | 4.2 + 7 | 242 bp | 44.3 |
| 4 | 4.3 + 7 | 114 bp | 54.8 |
| 5 | 5.1 + 7 | 276 bp | 69.3 |
| 5 | 5.2 + 7 | 535 bp | 72.4 |
| 5 | 5.3 + 7 | 337 bp | 74.9 |
| 5 | 5.4 + 7 | 221 bp | 74.9 |
| 6 | 6.1 + 7 | 203 bp | 6.4 |
| 6 | 6.2 + 7 | 293 bp | 6.9 |
| 6 | 6.3 + 7 | 185 bp | 68.4 |
| 6 | 6.4 + 7 | 377 bp | 78.6 |

TABLE 2

Overview of SEQ ID Nos

| SEQ ID No. | Primer | iSSR/RAPD | Sequence |
|---|---|---|---|
| 1 | 1.1 | iSSR | CAG GAA ACA GCT ATG ACA ATG CTT CTT CTT CTT C |
| 2 | 1.2 | iSSR | CAG GAA ACA GCT ATG ACG ACT ATA TAT ATA TAT ATA |
| 3 | 1.3 | iSSR | CAG GAA ACA GCT ATG ACA AAA GAG AGA GAG AGA |
| 4 | 1.4 | iSSR | CAG GAA ACA GCT ATG ACT AGG CTT CTT CTT CTT CTT C |
| 5 | 2.1 | iSSR | CAG GAA ACA GCT ATG ACC TCA TCC TCC TCC TCC |

TABLE 2-continued

Overview of SEQ ID Nos

| SEQ ID No. | Primer | iSSR/RAPD | Sequence |
|---|---|---|---|
| 6 | 2.2 | iSSR | CAG GAA ACA GCT ATG ACC GTC CTT CTT CTT CTT C |
| 7 | 2.3 | iSSR | CAG GAA ACA GCT ATG ACA GAT AGA GAG AGA GAG |
| 8 | 2.4 | iSSR | CAG GAA ACA GCT ATG ACG GTG AGA GAG AGA GAG AG |
| 9 | 3.1 | iSSR | CAG GAA ACA GCT ATG ACA GGT AGA GAG AGA GAG AG |
| 10 | 3.2 | iSSR | CAG GAA ACA GCT ATG ACC AAA CAC ACA CAC ACA C |
| 11 | 3.3 | iSSR | CAG GAA ACA GCT ATG ACC GAT CTC TCT CTC TCT CTC |
| 12 | 3.4 | iSSR | CAG GAA ACA GCT ATG ACT CCG CTT CTT CTT CTT CTT |
| 13 | 4.1 | iSSR | CAG GAA ACA GCT ATG ACC CAT CTT CTT CTT CTT C |
| 14 | 4.2 | iSSR | CAG GAA ACA GCT ATG ACT TTT CTT CTT CTT CTT C |
| 15 | 4.3 | iSSR | CAG GAA ACA GCT ATG ACG TTT GAG AGA GAG AG |
| 16 | 5.1 | iSSR | CAG GAA ACA GCT ATG ACC CTC ATC ATC ATC ATC A |
| 17 | 5.2 | iSSR | CAG GAA ACA GCT ATG ACT TGC ACA CAC ACA CAC A |
| 18 | 5.3 | iSSR | CAG GAA ACA GCT ATG ACG GGA GAG AGA GAG A |
| 19 | 5.4 | iSSR | CAG GAA ACA GCT ATG ACG CTC GAA GAA GAA GAA G |
| 20 | 6.1 | iSSR | CAG GAA ACA GCT ATG ACA GAC GAT GAT GAT GAT G |
| 21 | 6.2 | iSSR | CAG GAA ACA GCT ATG ACC CTC TGT TGT TGT TGT |
| 22 | 6.3 | iSSR | CAG GAA ACA GCT ATG ACT TGT GAG AGA GAG AGA G |
| 23 | 6.4 | iSSR | CAG GAA ACA GCT ATG ACG ATT GAT GAT GAT GAT GAT |
| 24 | 1.5 | iSSR | CAG GAA ACA GCT ATG ACA CCA TTC TTC TTC TTC |
|  | 7 | RAPD | Operon RAPD 10-mer kits A-01 t/m BH-20* |

*Eurofins MWG Operon, Anzingerstraβe 7a, 85560 Ebersberg Germany

The PCR reactions with the various primer combinations form the QTL-introgression fragments of a specific size (see Table 1). These DNA markers are characteristic for the QTLs involved. The combination of these DNA markers characterizing the QTL provides indisputable evidence of the presence of the QTL introgression from the *Plasmodiophora brassicae*-resistant source.

DEFINITIONS

Centimorgan (cM):
Unit for the genetic distance between markers, based on the number of cross-overs per hundred individuals.

DNA marker:
A DNA fragment which is linked to a gene or is located in a chromosome fragment at a known location on the genome, which is used to monitor heritability of this gene or this fragment.

Gel-electrophoresis:
Method for separating molecules (DNA, RNA, protein among others) on the basis of their size, shape or charge, in a matrix (agarose or polyacrylamide) under the influence of an electrical field.

Inbred generation (self-pollination):
Fertilization of an individual with its own pollen Introgression:
A chromosome fragment of a line which can be introduced by way of crossing into another line.

IRDye labels:
Infrared labels used for Licor imaging systems, the detection of which takes place at 700 nm or 800 nm.

Linkage Group:
A group of genes which are inherited in combination.

MARB:
Marker Assisted Recurrent Backcross: procedure in which a repeated backcrossing of a donor line with a quality line is supported with marker analysis, in order to select in each generation the plants which still have all QTLs for a determined resistance and genotypically correspond most to the quality line.

Monogenic:
Determined by one gene.

Polymerase Chain Reaction (PCR):
An in vitro amplification method for multiplying a specific DNA fragment. This synthesis reaction makes use of a minimum of one oligonucleotide primer which hybridizes with a DNA fragment, after which a polymerase amplifies the flanking region during successive temperature cycles.

Quantitative Trait Locus (QTL):

Chromosome region(s) which, coupled to one or more gene(s), together explain a quantitative trait.

Random Amplified Microsatellite Polymorphisms (RAMP):

DNA fingerprinting technique based on RAPD and iSSR primers with which polymorphisms between different DNA monsters are detected.

Random Amplified Polymorphic DNA (RAPD) primer:
A 10-mer with a "random" sequence, wherein the GC-content lies between 60% and 70% and wherein the primer ends are not self-complementary.

inter Simple Sequence Repeat (iSSR) primer:
A primer designed on the 5' end of an SSR (Single Sequence Repeat); a DNA fragment consisting of a repetition of 2 or 3 nucleotides with a 4 bp anchor at the 5' end Backcrossing:
Crossing of an individual with one of the original parents.

The invention claimed is:

1. A *Plasmodiophora brassicae*-resistant hybrid *Brassica oleracea* plant comprising in its genome three or more genetic factors imparting resistance, wherein the *Plasmodiophora brassicae*-resistance is from a plant with deposit number NCIMB 41685; wherein the genome includes a Quantitative Trait Locus 1 (QTL1) and a Quantitative Trait Locus 3 (QTL3) and a Quantitative Trait Locus 5 (QTL5),
   wherein QTL1 is characterized by a Random Amplified Microsatellite Polymorphism (RAMP) marker comprising a fragment of 294 bp with primer combination SEQ ID NOs:1 and 7;
   QTL3 is characterized by a RAMP marker comprising a fragment of 159 bp with primer combination SEQ ID NOs:9 and 7; and
   QTL5 is characterized by a RAMP marker comprising a fragment of 276 bp with primer combination SEQ ID NOs:16 and 7.

2. The plant as claimed in claim 1, wherein the QTL1, QTL3, and QTL5 are characterized by two or more RAMP markers.

3. The plant as claimed in claim 1, wherein the QTL1, QTL3, and QTL5 are characterized by three or more RAMP markers.

4. The plant as claimed in claim 1, wherein the QTL1, QTL3, and QTL5 are characterized by four or more RAMP markers.

5. The plant as claimed in claim 1, wherein the plant is a *Brassica* plant selected from the group consisting of *B. oleracea* convar. *botrytis* var. *botrytis* (cauliflower, romanesco broccoli), *B. oleracea* convar. *botrytis* var. *cymosa* (broccoli), *B. oleracea* convar. *botrytis* var. *asparagoides* (sprouting broccoli), *B. oleracea* convar. *oleracea* var. *gemnifera* (Brussels sprout), *B. oleracea* convar. *capitata* var. *alba* (white cabbage, oxheart cabbage), *B. oleracea* convar. *capitata* var. *rubra* (red cabbage), *B. oleracea* convar. *capitata* var. *sabauda* (savoy cabbage), *B. oleracea* convar. *acephala* var. *sabellica* (curly cale cabbage), *B. oleracea* convar. *acephela* var. *gongyloides* (turnip cabbage) and *B. oleracea* var. *tronchuda* syn. *costata* (Portuguese cabbage).

6. The plant as claimed in claim 1, wherein the plant is derived from a plant with the deposit number NCIMB 41685.

7. Seeds, fruits and/or plant parts of a *Brassica* plant as claimed in claim 1, which comprise QTL1, QTL3, and QTL5 as defined in claim 1.

* * * * *

```
                       SEQUENCE LISTING

<160> NUMBER OF SEQ ID NOS: 24

<210> SEQ ID NO 1
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 1.1"
      /organism="artificial sequences"

<400> SEQUENCE: 1
caggaaacag ctatgacaat gcttcttctt cttc                            34

<210> SEQ ID NO 2
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
      /note="primer 1.2"
      /organism="artificial sequences"

<400> SEQUENCE: 2
caggaaacag ctatgacgac tatatatata tatata                          36

<210> SEQ ID NO 3
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="primer 1.3"
      /organism="artificial sequences"

<400> SEQUENCE: 3
caggaaacag ctatgacaaa agagagagag aga                             33

<210> SEQ ID NO 4
<211> LENGTH: 37
<212> TYPE: DNA
<213> ORGANISM: artificial sequences
<220> FEATURE:
<221> NAME/KEY: source
<222> LOCATION: 1..37
<223> OTHER INFORMATION: /mol_type="DNA"
      /note="primer 1.4"
      /organism="artificial sequences"

<400> SEQUENCE: 4
caggaaacag ctatgactag gcttcttctt cttcttc                         37
```

```
<210> SEQ ID NO 5
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="primer 2.1"
      /organism="artificial sequences"

<400> SEQUENCE: 5
caggaaacag ctatgacctc atcctcctcc tcc                                33

<210> SEQ ID NO 6
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 2.2"
      /organism="artificial sequences"

<400> SEQUENCE: 6
caggaaacag ctatgaccgt ccttcttctt cttc                               34

<210> SEQ ID NO 7
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="primer 2.3"
      /organism="artificial sequences"

<400> SEQUENCE: 7
caggaaacag ctatgacaga tagagagaga gag                                33

<210> SEQ ID NO 8
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
      /note="primer 2.4"
      /organism="artificial sequences"

<400> SEQUENCE: 8
caggaaacag ctatgacggt gagagagaga gagag                              35

<210> SEQ ID NO 9
<211> LENGTH: 35
<212> TYPE: DNA
<213> ORGANISM: artificial sequences
<220> FEATURE:
<221> NAME/KEY: source
<222> LOCATION: 1..35
<223> OTHER INFORMATION: /mol_type="DNA"
      /note="primer 3.1"
      /organism="artificial sequences"

<400> SEQUENCE: 9
caggaaacag ctatgacagg tagagagaga gagag                              35
```

```
<210> SEQ ID NO 10
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 3.2"
      /organism="artificial sequences"

<400> SEQUENCE: 10
caggaaacag ctatgaccaa acacacacac acac                                  34

<210> SEQ ID NO 11
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
      /note="primer 3.3"
      /organism="artificial sequences"

<400> SEQUENCE: 11
caggaaacag ctatgaccga tctctctctc tctctc                                36

<210> SEQ ID NO 12
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
      /note="primer 3.4"
      /organism="artificial sequences"

<400> SEQUENCE: 12
caggaaacag ctatgactcc gcttcttctt cttctt                                36

<210> SEQ ID NO 13
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 4.1"
      /organism="artificial sequences"

<400> SEQUENCE: 13
caggaaacag ctatgaccca tcttcttctt cttc                                  34

<210> SEQ ID NO 14
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 4.2"
      /organism="artificial sequences"

<400> SEQUENCE: 14
caggaaacag ctatgactttt tcttcttctt cttc                                 34
```

<210> SEQ ID NO 15
<211> LENGTH: 32
<212> TYPE: DNA
<213> ORGANISM: artificial sequences
<220> FEATURE:
<221> NAME/KEY: source
<222> LOCATION: 1..32
<223> OTHER INFORMATION: /mol_type="DNA"
      /note="primer 4.3"
      /organism="artificial sequences"

<400> SEQUENCE: 15
caggaaacag ctatgacgtt tgagagagag ag                                   32

<210> SEQ ID NO 16
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 5.1"
      /organism="artificial sequences"

<400> SEQUENCE: 16
caggaaacag ctatgaccct catcatcatc atca                                 34

<210> SEQ ID NO 17
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 5.2"
      /organism="artificial sequences"

<400> SEQUENCE: 17
caggaaacag ctatgacttg cacacacaca caca                                 34

<210> SEQ ID NO 18
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="primer 5.3"
      /organism="artificial sequences"

<400> SEQUENCE: 18
caggaaacag ctatgacggg agagagagag a                                    31

<210> SEQ ID NO 19
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 5.4"
      /organism="artificial sequences"

<400> SEQUENCE: 19
caggaaacag ctatgacgct cgaagaagaa gaag                    34

<210> SEQ ID NO 20
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 6.1"
      /organism="artificial sequences"

<400> SEQUENCE: 20
caggaaacag ctatgacaga cgatgatgat gatg                    34

<210> SEQ ID NO 21
<211> LENGTH: 33
<212> TYPE: DNA
<213> ORGANISM: artificial sequences
<220> FEATURE:
<221> NAME/KEY: source
<222> LOCATION: 1..33
<223> OTHER INFORMATION: /mol_type="DNA"
      /note="primer 6.2"
      /organism="artificial sequences"

<400> SEQUENCE: 21
caggaaacag ctatgaccct ctgttgttgt tgt                     33

<210> SEQ ID NO 22
<211> LENGTH: 34
<212> TYPE: DNA
<213> ORGANISM: artificial sequences
<220> FEATURE:
<221> NAME/KEY: source
<222> LOCATION: 1..34
<223> OTHER INFORMATION: /mol_type="DNA"
      /note="primer 6.3"
      /organism="artificial sequences"

<400> SEQUENCE: 22
caggaaacag ctatgacttg tgagagagag agag                    34

<210> SEQ ID NO 23
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
      /note="primer 6.4"
      /organism="artificial sequences"

<400> SEQUENCE: 23
caggaaacag ctatgacgat tgatgatgat gatgat                  36

<210> SEQ ID NO 24
<211> LENGTH: 33
<212> TYPE: DNA
<213> ORGANISM: artificial sequences
<220> FEATURE:

```
<221>  NAME/KEY: source
<222>  LOCATION: 1..33
<223>  OTHER INFORMATION: /mol_type="DNA"
       /note="primer 1.5"
       /organism="artificial sequences"

<400>  SEQUENCE: 24 caggaaacag ctatgacacc attcttcttc ttc                                      33
```